United States Patent
Koros et al.

[11] Patent Number: 5,908,382
[45] Date of Patent: Jun. 1, 1999

[54] MINIMALLY INVASIVE RETRACTOR FOR INTERNAL MAMMARY ARTERY HARVESTING

[76] Inventors: Tibor B. Koros; Gabriel J. Koros, both of 610 Flinn Ave., Moorpark, Calif. 93021

[21] Appl. No.: 09/112,117

[22] Filed: Jul. 8, 1998

[51] Int. Cl.[6] .................................................. A61B 17/02
[52] U.S. Cl. ........................................... 600/232; 600/215
[58] Field of Search ..................................... 600/215, 228, 600/231, 232, 233, 234, 210, 216, 201

[56] References Cited

U.S. PATENT DOCUMENTS

| | | | |
|---|---|---|---|
| 2,670,732 | 3/1954 | Nelson | 600/234 |
| 4,254,763 | 3/1981 | McCready et al. | 600/228 |
| 4,467,791 | 8/1984 | Cabrera et al. | 600/234 |
| 4,726,356 | 2/1988 | Santilli et al. | 600/232 |
| 4,829,985 | 5/1989 | Couetil | 600/232 |
| 4,852,552 | 8/1989 | Chaux | 600/232 |
| 5,616,117 | 4/1997 | Dinkler et al. | 600/215 |
| 5,772,583 | 6/1998 | Wright et al. | 600/215 |

FOREIGN PATENT DOCUMENTS

| | | | |
|---|---|---|---|
| 356410 | 2/1990 | European Pat. Off. | 600/232 |
| 3834358 | 4/1990 | Germany | 600/232 |

Primary Examiner—Paul J. Hirsch
Attorney, Agent, or Firm—David O'Reilly

[57] ABSTRACT

An intermammary harvesting retractor comprised of a retractor frame having a fixed or stationary arm on one end of a crossbar and a movable arm mounted on the crossbar by a crank mechanism. The crank mechanism allows the movable arm to be adjusted toward or away from the stationary arm. A support tower is mounted on the free end of the retractor crossbar to allow the angle of the retractor to be adjusted after placement in an incision. The angular adjustment allows the upper portion of a patient's ribcage to be lifted to provide improved access and visualization to the intermammary artery. Adjustable lifter blades are provided on the movable arm to also adjust the lift angle of the upper ribcage. One embodiment has an adjustable lifter blade that can be adjusted after placement in the incision and adjustment of the angle of the retractor crossarm. Another embodiment employs a self-adjusting blade that is pivotally mounted in hangers provided on a lifter blade receiver coupling fitting on the end of the movable arm. The construction and arrangement of the invention allows the placement of the retractor and adjustment of the angle of the retractor by the support tower to lift and retract a patient's upper ribcage to allow improved visualization of the intermammary artery to harvest the intermammary artery for use in heart bypass procedures.

17 Claims, 6 Drawing Sheets

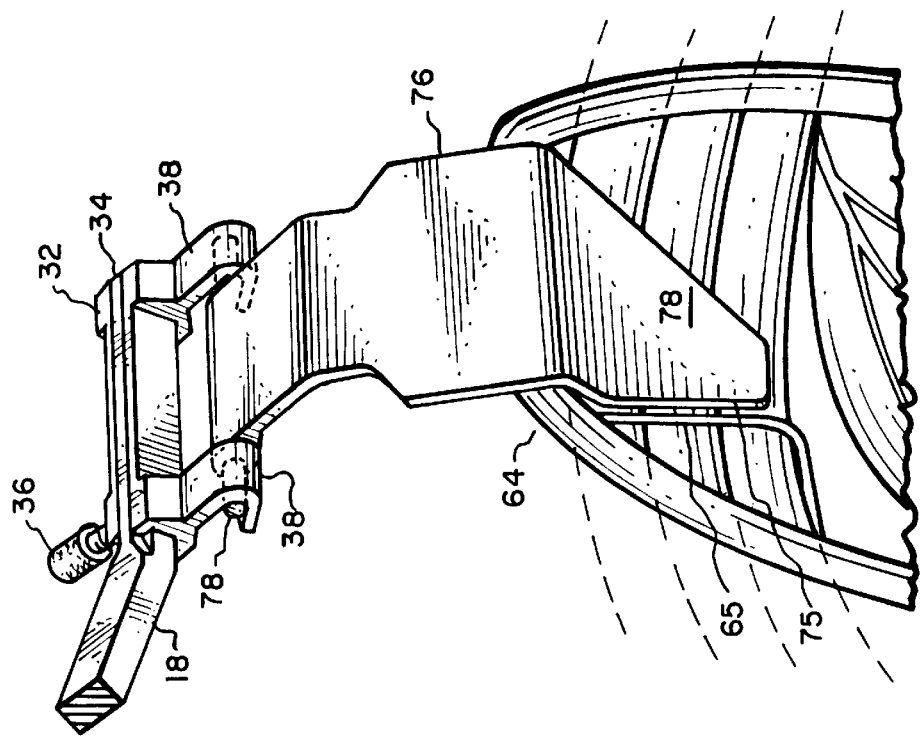
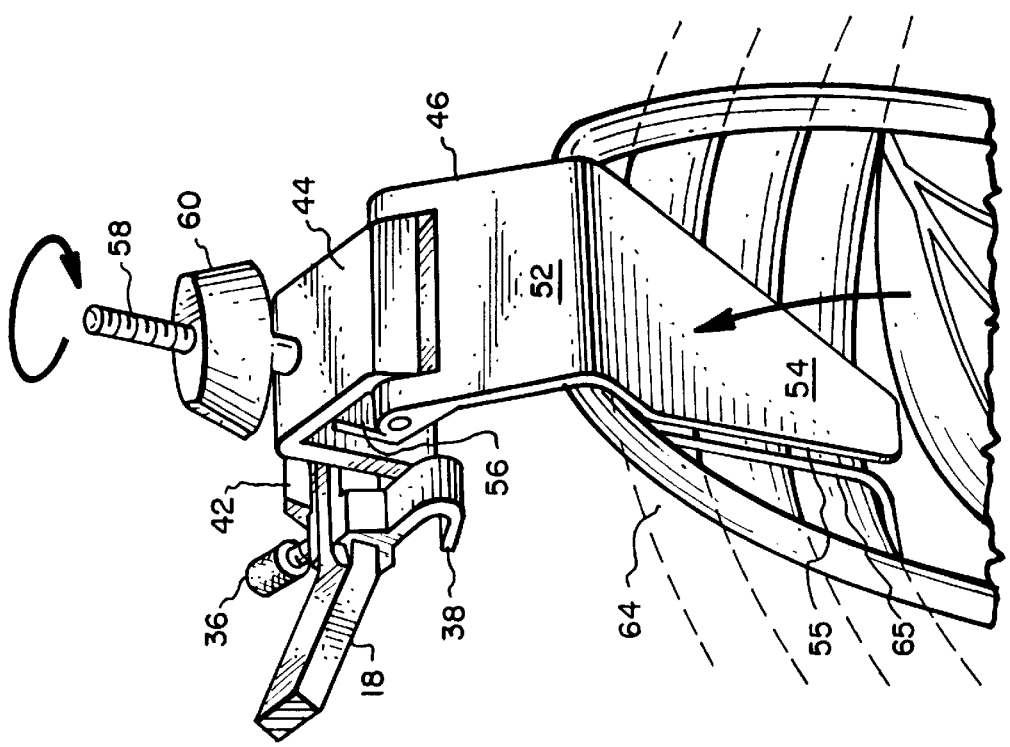

MINIMALLY INVASIVE RETRACTOR FOR INTERNAL MAMMARY ARTERY HARVESTING

BACKGROUND OF THE INVENTION

1. Field of the Invention

This invention relates to retractors for use in heart surgical procedures and more particularly relates to retractor for harvesting an internal mammary artery for use in heart bypass surgery.

2. Background Information

Surgical retractors are used in variety of surgical procedures such as open heart surgery for performing heart bypass operations. Doing these operations a suitable replacement for a clogged artery is needed. Often these arteries are taken from various parts of the human body but one commonly used artery is the internal mammary artery.

The internal mammary artery is found in the tissue beneath the ribcage immediately above and adjacent to the heart. A few centimeters in length is usually removed to be grafted to a clogged artery in the heart. Since this artery is embedded in the soft tissue beneath the ribcage, it is sometimes difficult to remove the graft.

To perform this procedure an incision must be made between ribs of the ribcage and the upper portion of the ribcage lifted to provide access to the internal mammary artery. However since the internal mammary artery traverses the soft tissue in the ribcage it is difficult to see. Presently available retractors do not allow a clear view or ready access to the internal mammary artery.

It is therefore one option of the present invention to provide a cardiovascular retractor for internal mammary artery harvesting.

Still another object of the present invention is to provide a cardiovascular retractor having a versatile design to accommodate patient anatomies and surgeon's techniques.

Still another object of the present invention is to provide a chest retractor having a support tower or stand that allows an improved angle of retraction for internal mammary artery visualization.

Still another object of the present invention is to provide chest retractor for internal mammary artery harvesting having a self-adjusting blade for lifting the ribcage.

Yet another object of the present invention is to provide a chest retractor for internal mammary artery harvesting having an adjustable lifter blade to adjust the angle of retraction for internal mammary artery visualization.

BRIEF DESCRIPTION OF THE INVENTION

The purpose of the prevent invention is to provide an improved chest retractor for use in internal mammary artery harvesting that provides an improved angle of retraction to allow internal mammary artery access and visualization.

The improved chest retractor is comprised of a slide retractor frame having a cross bar with a stationary or fixed arm at one end and a movable arm adjustable by a crank mechanism to read the spacing between the arms and the amount of retraction. The retractor frame is comprised of the cross bar having a rack gear and a stationary or fixed retractor arm at one end. A second movable retractor arm is adjustably attached to the cross bar and has a crank mechanism for moving the arm toward or away from the fixed arm to vary the spacing. The crank mechanism is disclosed and described in the U.S. Pat. No. 5,167,223 issued Dec. 1, 1992 to T. Koros et al and is incorporated herein by reference. Each arm has an end constructed for receiving a coupling on a blade for removably mounting a variety of retractor blades.

The fixed arm has a pair of flanges adapted to fit a slot in the coupling on a standard retractor blade. The coupling on the standard blade is formed with a flange having a socket for receiving the flanges on the free end of the fixed or stationary arm. The movable arm is also constructed with a pair of flanges that fit a lifter receiver coupling or for mounting a variety of retractor lifter blades. The lifter receiver or coupling also has a pair of curved hangers. A swinging, self-adjusting lifter blade is constructed with pins that fit the hangers to mount the self-adjusting blade on the lifter blade receiver which is mounted on the end of the movable arm. A screw clamps the blade mounting lifter blade receiver on the end of the movable arm.

The blade mounting lifter blade receiver has a configuration on the hangers for receiving the flange on an adjustable lifter blade. The mounting flange on the adjustable lifter blade hooks around the center portion of the blade mounting coupling between the hangers which assist in positioning the adjustable lifter blade.

The pins on the self-adjusting blade engage the hangers allowing the blade to swing freely so that the blade self adjusts when the tilt angle of the retractor is varied as will be described hereinafter.

In an optional but preferred embodiment an adjustable lifter blade assembly is provided in which a hinged swinging deep retractor lifter blade has a mechanism for manually adjusting the angle of the blade. The adjustable lifter blade assembly is comprised of the blade mounting coupling having a configuration for receiving a blade mounting flange on the adjustable lifter blade. The blade mounting flange fits between the hangers and wraps around the center portion of the lifter blade mounting coupling. The adjustable blade is hingedly mounted on the end of a flange plate on the blade mounting flange. The adjustable lifter blade is mounted by a pin passing through a pair of ears on the blade which passes through a bore in the end of the flange plate.

An extension on the adjustable lifter blade forms a ledge beneath flange plate. A screw mounted on the ledge extends through the flange plate. A wing nut on the screw adjusts the spacing between the ledge and the flange plate to adjust the angle of the swinging or hingedly mounted adjustable lifter blade.

The hingedly mounted adjustable lifter blade has a curved portion extending to a tapered tongue constructed to fit beneath the ribcage of a patient. One side of the tapered tongue is cut at an oblique angle to align with the intermammary artery. This oblique angle of the tapered tongue allows the surgeon to place the blade along the intermammary artery but without interfering with the surgical procedure to harvest the artery.

A tower or stand is provided to adjust the angle of the retractor when placed in an incision to allow the upper portion of the chest to be lifted so that a surgeon may see the intermammary artery in the tissue beneath the ribcage. The tower is comprised of a support bar mounted on the free end of the retractor cross bar opposite the stationary or fixed arm and a support shaft or tower adjustably connected to the support bar with a connecting clamp. A footpad on the end of the support tower rests on the surface of the patient's chest when the intermammary artery harvesting retractor is placed in the incision. Adjustment of the height of the tower allows the angle of the retractor to vary. Raising the tower lifts the free end of the cross bar adjusting the angle of the retractor allowing the upper ribcage to be lifted for improved access and visualization of the intermammary artery. The self-adjusting lifter blade connected to the lifter blade receiver coupling swivels or pivots in its mounting to self adjust to the angle of the retractor.

More flexibility in adjusting the angle of the retractor visualization of the intermammary artery is provided with the combination of the adjustable tower and an adjustable lifter blade. The tower may be adjusted to adjust the angle of the retractor to lift the upper ribcage to provide access and visualization to the intermammary artery. The adjustable lifter blade can then also be adjusted to lift the ribcage. The tower and the adjustable lifter blade can be alternately adjusted until the proper angle of access and visualization is provided to the surgeon for harvesting an intermammary artery.

The retractor is placed in an incision with the arms substantially closed and a standard blade mounted on the stationary fixed arm and the self-adjusting swinging lifter blade or adjustable lifter blade mounted on the movable arm. The crank mechanism is then operated to spread the incision sufficiently to provide access to the intermammary artery. The tower may then be adjusted to increase the angle of the retractor to lift the upper ribcage of the patient providing improved visualization and access to the intermammary artery. If the adjustable lifter blade is used it may then be adjusted with the thumbscrew to improve the angle of access.

The above and other novel features of the invention will be more fully understood from the following detailed description and the accompanying drawings, in which:

BRIEF DESCRIPTION OF THE DRAWINGS

FIG. 3 illustrates the adjusting of the adjustable lifter blade to provide improved access and visualization of the intermammary artery.

FIG. 4 is a isometric view of an alternate embodiment using a self-adjusting blade mounted on hangers on lifter blade receiver or coupling.

DETAILED DESCRIPTION OF THE INVENTION

Figure 1:
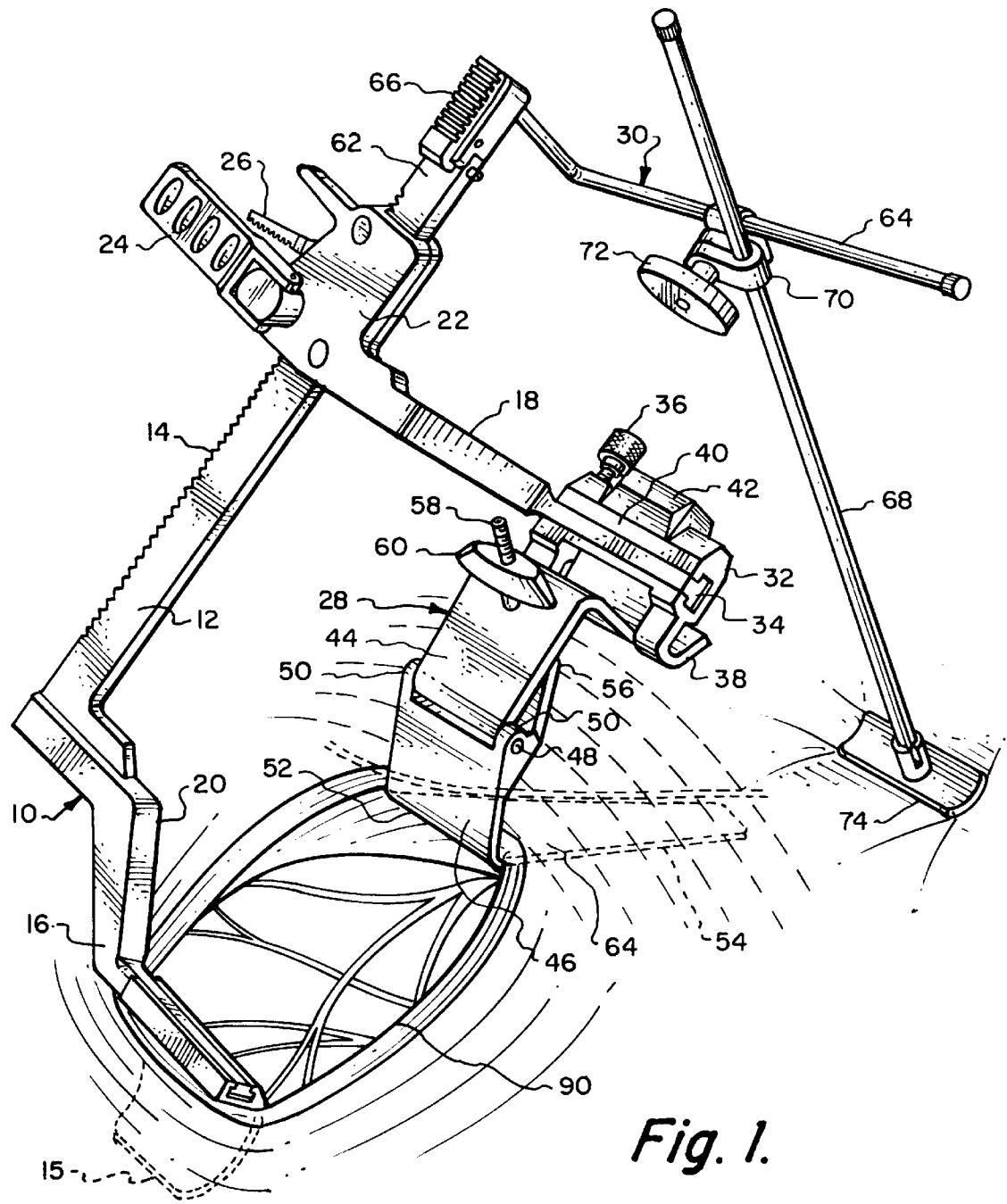
FIG. 1 is an isometric view illustrating the intermammary artery harvesting retractor according to the invention.

A retractor for placement in incision for harvesting an intermammary artery is shown generally in the isometric view of FIG. 1. Intermammary harvesting retractor 10 is comprised of cross bar 12 having a rack gear 14, a stationary or fixed arm 16 for mounting a standard blade 15 and movable arm 18. Stationary arm 16 is provided with an offset 20 to accommodate adjustable lifter blades attached to the end of movable arm 18 as will be described hereinafter.

The position of movable arm 18 relative to stationary or fixed arm 18 is adjusted by means of a crank mechanism 22. Crank mechanism includes a gear (not shown) engaging gear rack 14 that is operated by crank handle 24 as is disclosed and described in U.S. Pat. No. 5,167,223 issued Dec. 1, 1992 to T. Koros et al and incorporated herein by reference. A quick release locking mechanism 26 locks the movable arm 18 in an adjusted position and allows the arms to be quickly closed prior to placement in an incision. By closing the handles of quick release locking mechanism 26 the gear is released from rack gear 14 allowing movable arm 18 to be quickly moved along crossbar 12 toward fixed arm 16. When released the gear is then again engaged on rack gear 14 for adjustment by rotation of crank 24.

A very important function of the retractor of the present invention is to provide improved access and visualization for harvesting intermammary artery used in heart bypass surgery. A section of the intermammary artery is removed and then used for bypassing a blockage of an artery supplying blood to the heart. This allows the surgeon to perform heart bypass surgery with one operation and through a single incision rather than other methods where arteries are taken from other parts of the body requiring two or more separate surgical procedures. However the intermammary artery is not easily accessible because if is in the tissue just beneath the ribcage. Presently harvesting this intermammary artery is a difficult and time-consuming task which is disadvantageous because it is important that surgical procedures be completed efficiently and as quickly as possible to minimize trauma to the patient. Therefore the retractor of the present invention has been created to provide improved access and visualization of the intermammary artery.

To achieve this result the retractor of the present invention provides a construction that allows the upper ribcage to be lifted providing an improved access and view to the tissue just beneath the ribcage. This improved access is provided by a retractor having adjustable blade assembly 28 and an adjustable tower or stand 30 which will be described in greater detail hereinafter. Adjustable lifter blade assembly 28 is comprised of a lifter blade receiver coupling 32 fitting on flanges 34 on the end of movable arm 18. Adjustable lifter blade coupling 32 has a clamping screw 36, a pair of hangers 38, and a center portion 40 for receiving adjustable lifter blade mounting flange 42.

Adjustable lifting blade mounting flange 42 has flange plate 44 for hingedly mounting adjustable lifter blade 46 by pin 48 fitting through ears 50 and an aperture in the end of flange plate 44 allowing lifter blade 46 to freely swing about the axis of pin 48. Hingedly mounted adjustable lifter blade 46 has a curved portion 52 and a tapered blade portion 54 that will be described in greater detail hereinafter. Adjustable lifter blade extension 56 provides a ledge for mounting adjusting screw 58 which receives a wing nut 60. Adjustment of wing nut 68 on screw 58 varies the spacing between ledge 56 and flange plate 44 to adjust the angle of adjustable lifter blade 46 as will be described in greater detail hereinafter.

To lift the upper ribcage the angle of retractor 10 must be adjusted. The angle of retractor 10 is adjusted by lifting free end 62 of crossbar 12 which in turn lifts the upper portion 64 of a patient's ribcage allowing the surgeon improved access and a better visibility of the tissue beneath ribcage. Adjustment of the free end 62 of crossbar 12 is provided by support tower assembly 30 comprised of support bar 64 mounted on free end 62 of crossbar 12 by clamp 66 and support tower or stand 68 mounted on support bar 64 by clamp 70 clamped by thumbscrew 72. Support stand or tower 68 has a footpad 74 that rests on the patient's chest. The length and position of support tower or stand 68 is adjusted by loosening thumbscrew 72 and lifting free end 62 of crossbar 12 to lift upper ribcage 64 and is then reclamped by tightening thumbscrew 72 as will be described in greater detail hereinafter.

Figure 2:
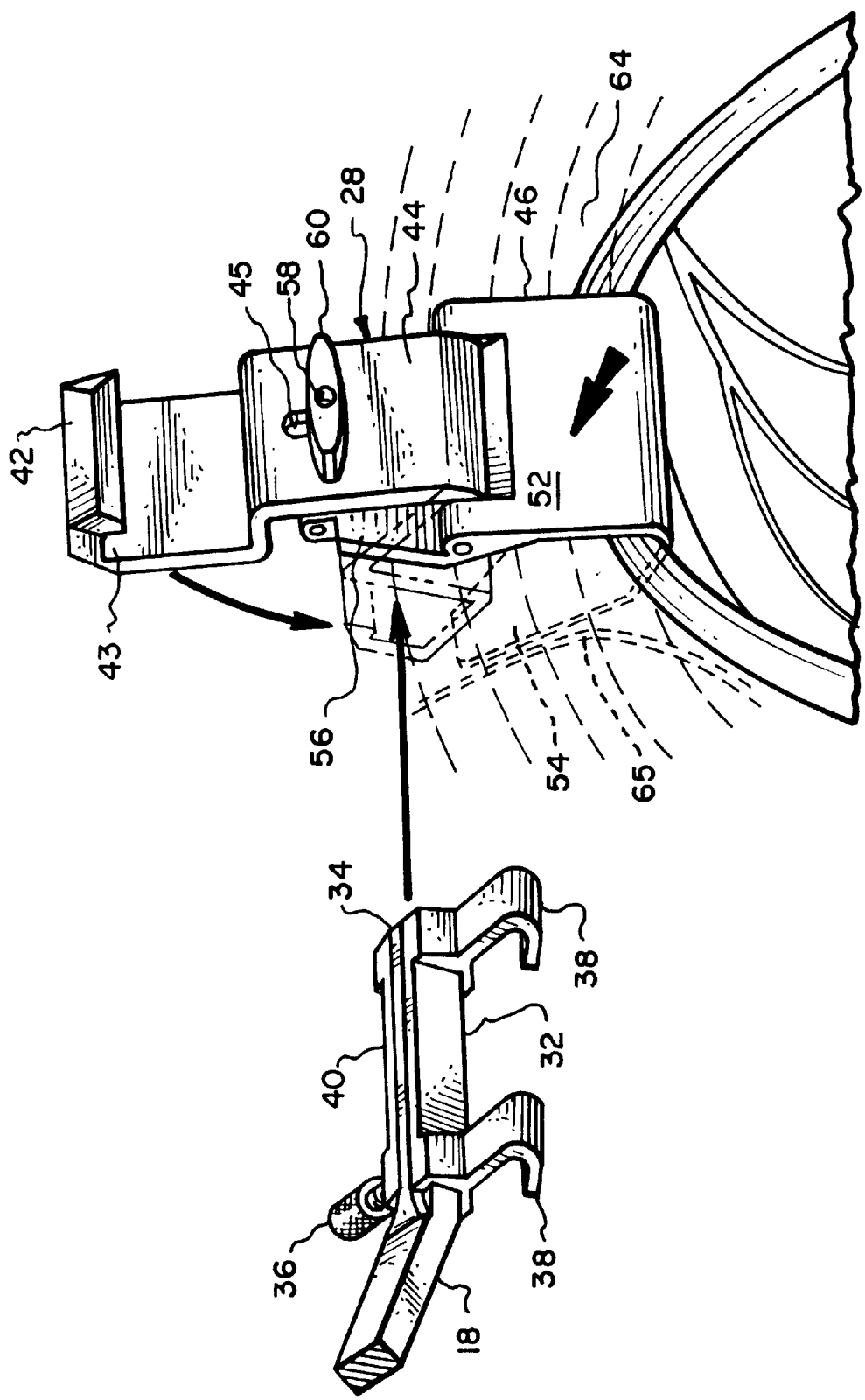
FIG. 2 illustrates the mounting of an adjustable lifter blade on the movable arm of the intermammary artery retractor.

The construction of adjustable lifter blade and its operation is illustrated in FIG. 2. Swinging adjustable lifter blade 28 has a flange 42 forming a groove 44 that fits around center portion 40 of lifter blade receiver coupling 32 that slides on flange end 34 of movable arm 18 and is clamped by screw 36. Adjustable lifter blade flange 42 has a plate 44 having a slot 45 for receiving screw thread 58 mounted on ledge 56 provided by an extension of swinging adjustable lifter blade 46. Wingnut 60 allows the spacing between ledge 56 and flange plate 44 to be varied to vary the angle of hinged adjustable lifter blade 46 as is illustrated in FIG. 3.

With retractor 10 placed in an incision, lifter blades to lift the upper chest to provide access to intermammary artery 65 that is in tissue just beneath ribcage 64. As shown in FIG. 3, adjustable lifter blade 46 fits in incision beneath upper ribcage 64. As the tilt angle of the retractor is increased adjustable lifter blade 46 may be adjusted by rotating wingnut 60 on threaded screw 58 varying the space between ledge 56 and flange plate 44 to increase the angle of the upper ribcage 64 providing improved access and visualization of the intermammary artery 65.

In some cases it may be suitable to provide a self-adjusting lifter blade 76 that is attached to movable arm 18 by pins 78 that engage hangers 38 on lifter blade receiver coupling 32. This arrangement allows self-adjusting blade 76 to swing freely on lifter blade receiver coupling 32 to self adjust according to the angle of the retractor and thus movable arm 18. As the free end 62 (FIG. 1) of retractor 10 is lifted, self-adjusting lifter blade 76 adjusts to lift the upper portion of ribcage 64 providing improved access to intermammary artery 65 allowing the surgeon to more easily and readily harvest a section of the artery.

The unique feature of each of the adjustable lifter blade 46 and self-adjusting blade 76 is the provision of a tongue on the blades that allow precise alignment with the intermammary artery. As shown in FIG. 3, tongue 54 on adjustable lifter blade 46 is tapered and has the left side 55 cut at an oblique angle to be aligned with intermammary artery 65. Likewise self-adjusting lifter blade 76 has a tongue 78 having the left side 75 cut at an oblique angle also to be aligned with intermammary artery 65. This precise oblique angle allows the intermammary harvesting retractor to be placed properly with minimum interference and improve access to the intermammary artery.

Figure 5:
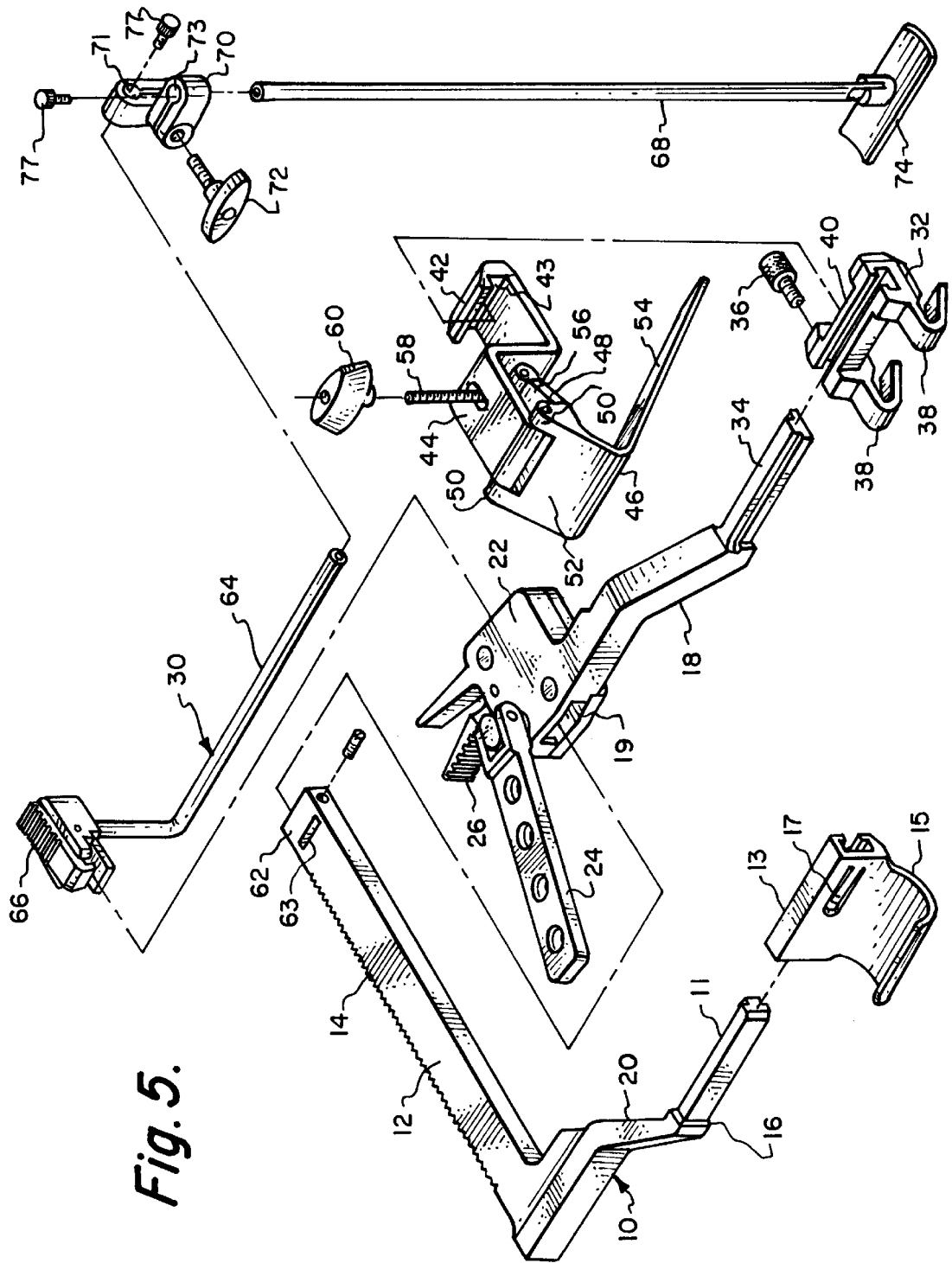
FIG. 5 is an exploded view illustrating an assembly of the intermammary artery retractor.

The assembly of the intermammary artery harvesting retractor is illustrated in an exploded view of FIG. 5. Crossbar 12 and fixed arm 16 form a frame for retractor 10. Movable arm 18 is mounted on crossbar 12 by engaging slot 19 in crank mechanism 22 so that gear 14 engages gear (not shown) in gear mechanism 22. Release of lock 26 allows movable arm 18 to slide freely on crossbar 12 toward stationary or fixed arm 16. Release of lock mechanism 26 engages gear in gear rack 14 for adjustment by crank arm 24. Rotation of crank arm 24 moves movable arm 18 away from stationary arm 16 which remains locked in the adjusted position. A standard blade 15 is mounted on end 11 of fixed arm 16 by engaging a C-shaped socket in coupling 13. Leaf spring 17 in coupling 13 firmly holds standard blade 15 on fixed arm 16. The ends of fixed arm 16 and movable arm are found with inverted T-shaped tongues 11 and 34 that engage C-shaped grooves or sockets on blade 15 or blade mounting coupling 32.

Adjustable lifter blades are mounted on movable arm 18 by lifter blade receiving C-shaped socket in coupling 32 that engages flange end or inverted T-shaped tongue 34 of movable arm 18 and is locked in place by screw 36. Adjustable lifter blade 46 is then fitted around the center portion 40 of lifter blade receiver coupling 32 with groove 44 of blade mounting flange 42 fitting around center portion 40 between hangers 38 which properly position blade mounting flange of adjustable lifter blade 46. Wingnut 60 is then mounted on threaded screw 58 for adjusting the position of adjustable lifter blade 46 by varying the spacing between ledge 56 formed by an extension on adjustable lifter blade 46 and flange plate 44.

Adjustable tower assembly 30 is assembled by clamp 66 fitted on end 62 of crossbar 12 with a tab engaging a slot 63. This securely locks support bar 64 on retractor 10. Support tower or stand shaft 68 is then attached to support arm 64 by clamp 70 having holes 71 and 73 for receiving ends of support bar 64 and tower shaft 68 respectively. Screws 77 in the ends of support bar 64 and tower shaft 68 prevent clamp 70 from slipping off the respective shafts. Thumbscrew 72 securely clamps tower shaft 68 on support bar 64 and allows an adjustment of the position and length. Loosening of thumbscrew 72 allows horizontal adjustment along support bar 64 and vertical adjustment of tower shaft 68.

Figure 6:
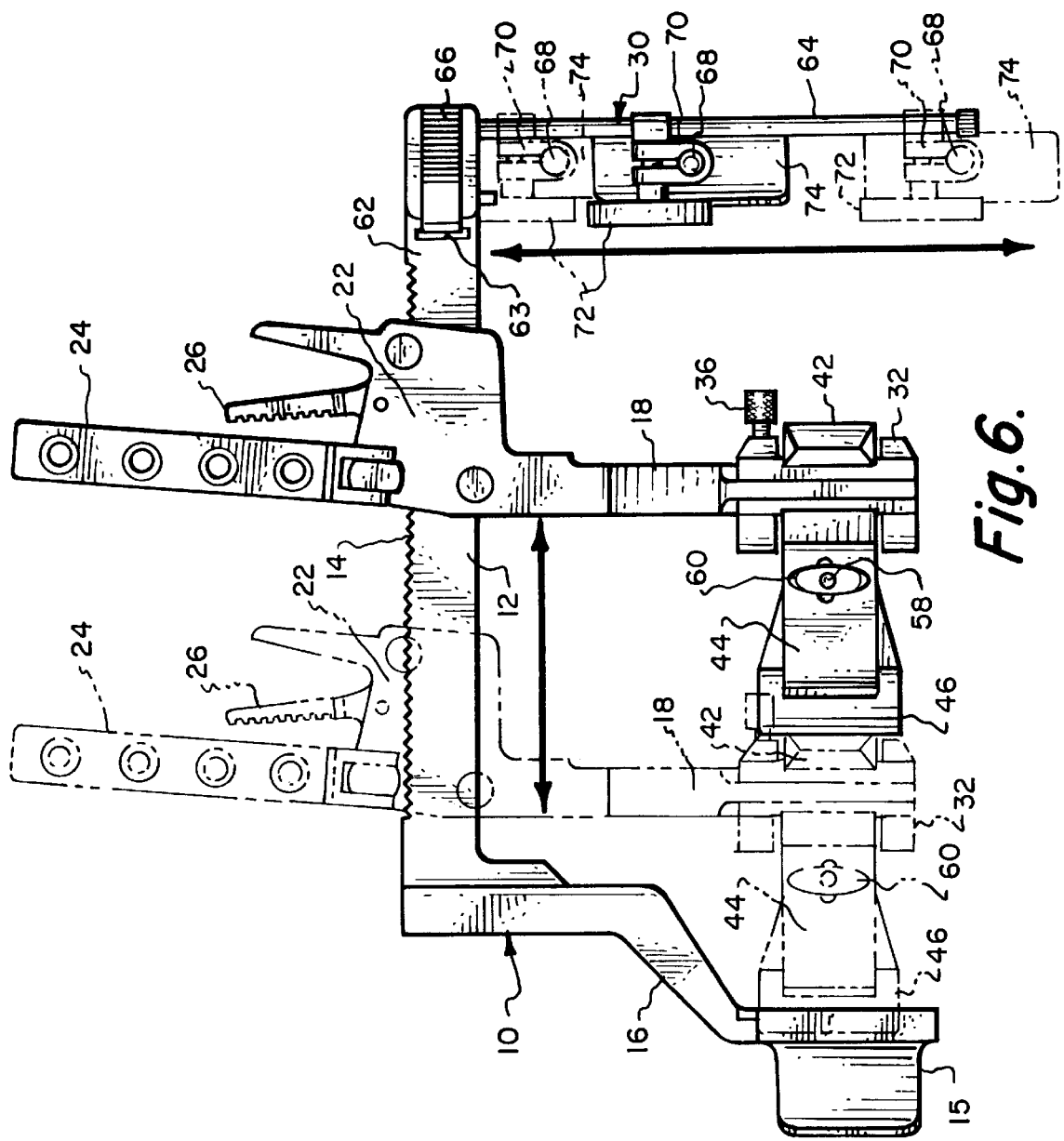
FIG. 6 is a top view of the intermammary artery retractor illustrating placement in an incision and adjustment to spread or retract the tissue.
Figure 7:
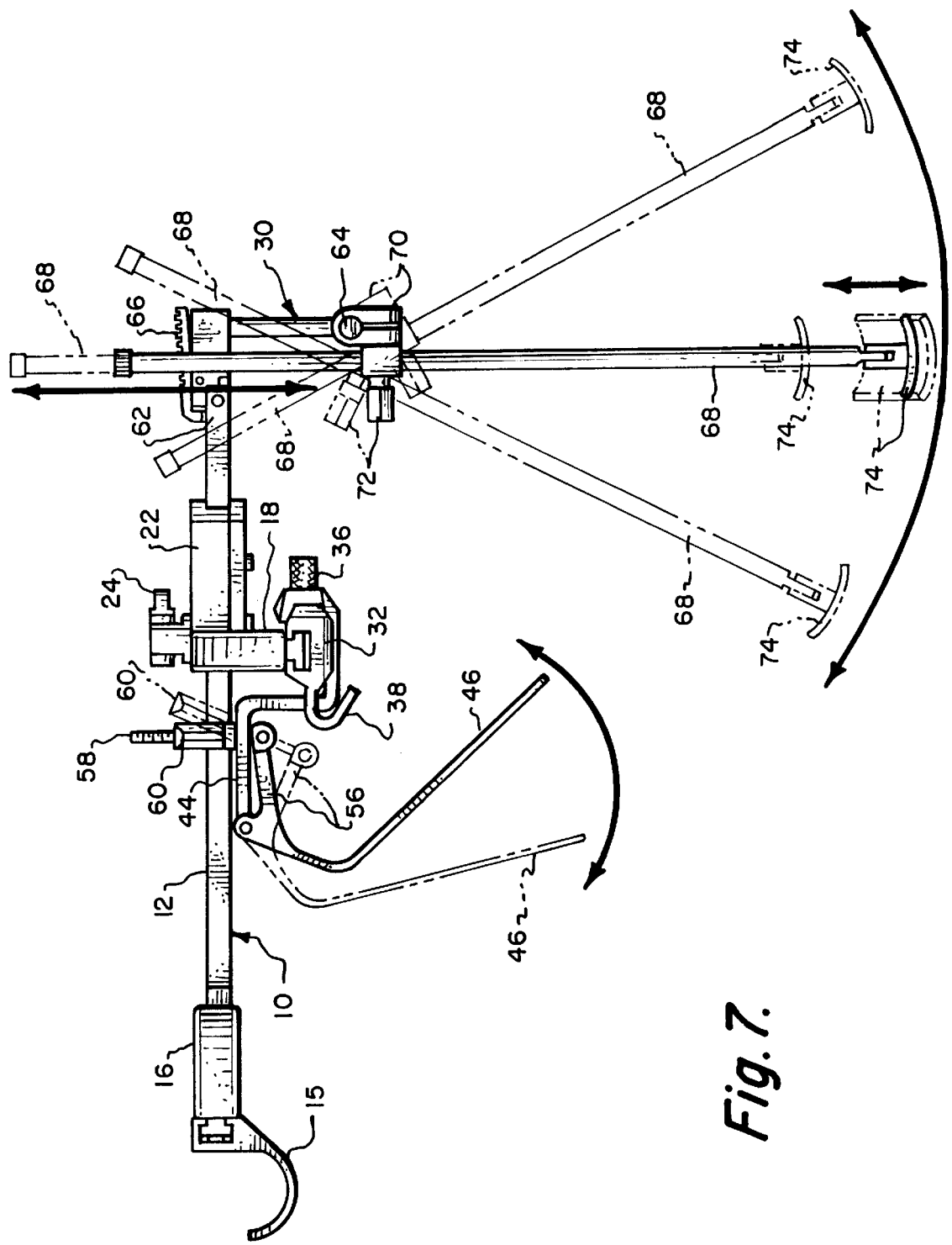
FIG. 7 illustrates the adjustments to the intermammary harvesting retractor to vary the angle of the adjustable lifter blade and the angle or position of the lifting tower.

The placement of the intermammary harvesting retractor and adjustments are illustrated in FIGS. 6 and 7. Intermammary harvesting retractor 10 is assembled as shown in FIG. 5 and movable arm 18 released by closing locking mechanism 26 to allow movable arm 18 to slide to a fully closed position adjacent stationary of fixed arm 16 illustrated in phantom in FIG. 6. Standard blade 15 and adjustable lifter blade 46 are then placed in the incision and crank arm 24 rotated to operate crank mechanism 22 to move movable arm 18 away from stationary arm to retract the ribcage and tissue to spread incision 90 as shown in FIG. 1. Tower assembly is then adjusted by loosening thumbscrew 72 allowing support tower 68 to be moved horizontally along support bar 64 as well as vertically in clamp 70. Free end 62 of retractor 10 is lifted to lift upper ribcage 64 and support tower 68 adjusted vertically and horizontally to hold the retractor frame at the precise adjusted angle. Support tower assembly 30 is then securely clamped by tightening thumbscrew 72. Adjustments of support tower assembly 30 are illustrated in FIG. 7. Support tower can be adjusted horizontally along support bar 64 vertically in support clamp 70 or an angular adjustment may be made by rotating clamp 70 on support bar 64 as shown in the two positions illustrated in phantom. This permits wide variety of adjustments of retractor 10 to improve access and visualization of the intermammary artery beneath ribcage 64.

Adjustable lifter blade 46 may now be adjusted by rotating wingnut 60 on threaded shaft 58 to vary the spacing between flange plate 44 and ledge 56 extending from adjustable lifter blade 46. Support tower assembly 30 and adjustable lifter blade assembly 28 may be alternately adjusted until optimum position of retractor 10 is achieved and in the best possible access to the intermammary artery 65 beneath upper portion of ribcage 64 is achieved.

In some cases self-adjusting lifter blade 76 may be substituted for adjusted lifter blade 46. Self-adjusting lifter blade 76 will be mounted on movable arm 78 by pins 78 that engage hangers 38 allowing self-adjusting lifter blade 76 to pivot freely on movable arm 18. As the angle of free end 62 of retractor 10 is increased by adjustment of tower assembly 30 self-adjusting lifter blade will reposition itself by pivoting on hangers 38.

Thus there has been disclosed an intermammary harvesting retractor that provides retractor adjustments allowing optimum access and visualization of the intermammary artery. The retractor is comprised of a fixed arm and a movable arm which has an adjustable lifter blade to lift the upper ribcage to view the intermammary artery. A support tower assembly on the free end of the retractor crossbar allows the tilt angle of the retractor to be adjusted to lift the upper ribcage to view the underside tissue providing improved access to the intermammary artery. The support tower has a support shaft whose length and position can be varied as necessary that cooperates with an adjustable lifter blade to lift and displace the upper portion of the ribcage to view the underside of the tissue containing the intermammary artery. In one embodiment an adjustable lifter blade is mounted on the movable arm. In a second embodiment a self-adjusting lifter blade is pivotally mounted on the movable arm.

Obviously many modifications and variations of the invention are possible in light of the above teachings. It is therefore understood that the full scope of the invention is not limited to the details disclosed herein but only by the claims appended hereto and may be practiced otherwise as specifically described.

What is claimed is:

1. An intermammary artery access retractor comprising;
   a frame having a crossbar, a fixed retractor arm and a movable retractor arm, said movable arm being movable toward or away from the fixed arm;
   a standard retractor blade mounted on said fixed arm;
   an adjustable lifter blade mounted on said movable retractor arm;
   tilting means for tilting said retractor to lift a portion of a ribcage to provide improved access to the intermammary artery.

2. The retractor according to claim 1 in which said adjustable lifter blade comprises;
   blade mounting means;
   an adjustable lifter blade hingedly attached to said blade mounting means;
   angle adjusting means for adjusting the angle of retraction of said adjustable lifter blade; whereby said blade lifts an upper portion of the ribcage to provide improved access and visibility of the intermammary artery.

3. The retractor according to claim 2 in which said angle adjusting means comprises; a flange on said blade mounting means; and a screw in said flange engaging a surface of said hingedly mounted blade; whereby rotation of said screw adjusts the angle of said blade on said retractor.

4. The retractor according to claim 3 in which said adjustable lifter blade has a curved portion and a tongue portion; said tongue portion being tapered toward a tip.

5. The retractor according to claim 4 in which said tongue on said adjustable lifter blade has an oblique edge constructed to be aligned with the intermammary artery.

6. The retractor according to claim 1 in which said retractor tilting means comprises an adjustable support tower attached to a free end of said crossbar on said retractor frame for raising or lowering the retractor frame to raise an upper portion of the ribcage to provide improved access and visibility of said intermammary artery.

7. The retractor according to claim 6 in which said adjustable support tower comprises a support bar mounted on a free end of said retractor crossbar;
   a support shaft;
   clamp means for clamping and adjustably positioning said support shaft on said support bar to raise or lower said retractor.

8. The retractor according to claim 7 including a footpad on an end of said support shaft.

9. The retractor according to claim 3 in which said retractor tilting means comprises an adjustable support tower attached to a free end of said crossbar on said retractor frame for raising or lowering the retractor frame to raise an upper portion of the ribcage to provide improved access and visibility of said intermammary artery.

10. The retractor according to claim 9 in which said adjustable support tower comprises a support bar mounted on a free end of said retractor crossbar;
    a support shaft;
    clamp means for clamping and adjustably positioning said support shaft on said support bar to raise or lower said retractor.

11. The retractor according to claim 10 including a footpad on an end of said support shaft.

12. The retractor according to claim 11 including means for pivotally mounting said adjustable lifter blade on said movable retractor arm.

13. The retractor according to claim 12 in which said pivotally mounting means comprises; a lifter blade receiver coupling; a pair of hangers on said lifter blade receiver coupling; a pair of pins on said self-adjusting lifter blade engaging said hangers.

14. The retractor according to claim 1 in which said adjustable lifter blade is self-adjusting.

15. The retractor according to claim 14 including mounting means mounting said self-adjusting lifter blade so that said self-adjusting lifter blade swings freely on said movable retractor arm.

16. The retractor according to claim 15 in which said mounting means comprises a pair of hangers mounted on said movable retractor arm and a pair of pins on said self-adjusting lifter blade engaging said pair of hangers.

17. The retractor according to claim 16 in which said retractor arms have inverted T-shaped tongues on their ends for frictionally engaging C-shaped sockets on a retractor blade.

* * * * *